United States Patent
Hao et al.

(10) Patent No.: US 8,883,207 B2
(45) Date of Patent: Nov. 11, 2014

(54) CONTROLLED RELEASE CARVEDILOL FORMULATION

(75) Inventors: Wei-Hua Hao, Taipei (TW); Tsung-Hsin Lin, Taipei (TW); Ta-Chien Lu, Taipei (TW)

(73) Assignees: TSH Biopharm Corporation Ltd., Taipei (TW); Innopharmax, Inc., Taipei (TW)

( * ) Notice: Subject to any disclaimer, the term of this patent is extended or adjusted under 35 U.S.C. 154(b) by 18 days.

(21) Appl. No.: 13/498,751
(22) PCT Filed: Sep. 29, 2010
(86) PCT No.: PCT/CN2010/077466
§ 371 (c)(1),
(2), (4) Date: Jun. 5, 2012
(87) PCT Pub. No.: WO2011/038683
PCT Pub. Date: Apr. 7, 2011

(65) Prior Publication Data
US 2012/0245212 A1      Sep. 27, 2012

Related U.S. Application Data

(60) Provisional application No. 61/246,804, filed on Sep. 29, 2009.

(51) Int. Cl.
| | |
|---|---|
| A61K 9/22 | (2006.01) |
| A61K 9/00 | (2006.01) |
| A61K 9/24 | (2006.01) |
| A61K 9/20 | (2006.01) |
| A61K 31/403 | (2006.01) |

(52) U.S. Cl.
CPC ............... *A61K 9/2027* (2013.01); *A61K 9/209* (2013.01); *A61K 9/2054* (2013.01); *A61K 31/403* (2013.01)
USPC .......................................... 424/468; 424/400

(58) Field of Classification Search
None
See application file for complete search history.

(56) References Cited

U.S. PATENT DOCUMENTS 5,407,687 A * 4/1995 Coffin et al. ................... 424/472
5,939,385 A * 8/1999 Labroo et al. ................ 424/94.5

(Continued)

FOREIGN PATENT DOCUMENTS

| CN | 1285738 A | 2/2001 |
|---|---|---|
| CN | 1525855 A | 9/2004 |

(Continued)

OTHER PUBLICATIONS

International Search Report, dated Jan. 6, 2011, issued in corresponding International Application No. PCT/CN2010/077466.

(Continued)

*Primary Examiner* — Carlos Azpuru
*Assistant Examiner* — Casey Hagopian
(74) *Attorney, Agent, or Firm* — Birch, Stewart, Kolasch & Birch LLP

(57) ABSTRACT

A controlled release carvedilol formulation for less frequent, preferably once daily administration is described. The controlled release formulation comprises a therapeutically effective amount of carvedilol or a pharmaceutically acceptable salt thereof, a matrix forming polymer, a solubility enhancer and a pharmaceutically acceptable carrier. In one embodiment, a controlled release formulation having a therapeutically effective amount of carvedilol is contained in two or more subunits having different release profiles. The controlled release formulation is usable in the treatment and/or prophylaxis of one or more conditions such as cardiovascular disorders.

14 Claims, 6 Drawing Sheets

(56) References Cited

U.S. PATENT DOCUMENTS

| | | |
|---|---|---|
| 2002/0182256 A1 | 12/2002 | Oh |
| 2003/0035836 A1 | 2/2003 | Shanghvi et al. |
| 2004/0198812 A1 | 10/2004 | Bubendorf et al. |
| 2006/0099245 A1* | 5/2006 | Kumar et al. ............ 424/451 |
| 2008/0292695 A1 | 11/2008 | Arnold et al. |

FOREIGN PATENT DOCUMENTS

| | | | |
|---|---|---|---|
| JP | 2004-534031 A | 11/2004 |
| WO | WO 03/097018 A1 | 11/2003 |
| WO | WO 2004/096182 A1 | 11/2004 |
| WO | 2005-507899 A | 3/2005 |
| WO | WO 2005/051325 A2 | 6/2005 |
| WO | WO 2009/110004 A1 | 9/2009 |

OTHER PUBLICATIONS

Extended European Search Report, dated Jul. 15, 2014, for European Application No. 10819912.6.

* cited by examiner

CONTROLLED RELEASE CARVEDILOL FORMULATION

CROSS REFERENCE TO RELATED APPLICATIONS

This application is the National Phase of PCT/CN2010/077466 filed on Sep. 29, 2010, which claims priority under 35 U.S.C. 119(e) to U.S. Provisional Application No. 61/246,804 filed on Sep. 29, 2009, all of which are hereby expressly incorporated by reference into the present application.

FIELD OF THE INVENTION

The present invention relates to a controlled released carvedilol formulation for less frequent, preferably once daily administration. More specifically, the present invention also relates to the use of such controlled released formulation in the treatment and/or prophylaxis of one or more conditions in subjects suffering from, for example, cardiovascular disorders

BACKGROUND OF THE INVENTION

The chemical name of carvedilol is ((±)1-(carbazol-4-yloxy-3-[[2-(o-methoxyphenoxy)ethyl]-amino]-2-propanol), the structure of which is shown as follows:

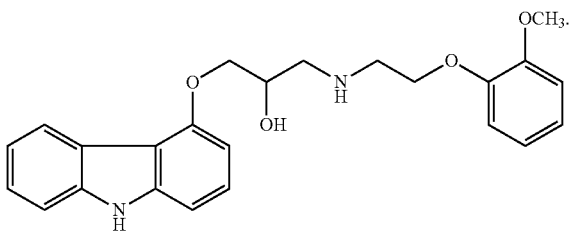 [SMILES: COc1ccccc1OCCNCC(O)COc1cccc2[nH]c3ccccc3c12]

Carvedilol is a nonselective beta-adrenergic blocking agent with vasodilatory actions due to alpha-adrenoreceptor blockage. It is commonly used for the treatment of cardiovascular diseases, such as hypertension, congestive heart failure or left ventricular dysfunction following myocardial infarction. The anti-hypertensive actions of carvedilol result primarily from alpha-adrenoreceptor blockage, whereas the beta-adrenergic blocking action prevents the unwanted side effect, mainly reflex tachycardia, when used in the treatment of hypertension.

However, carvedilol has certain disadvantages in the treatment of medical conditions. For example, carvedilol is known to have solubility and stability problems and poor bioavailability. It is a weak base, so the solubility depends on the pH value. At pH values in the pharmaceutically relevant range of 1 to 8, the solubility of carvedilol in aqueous media increases from about 0.01 mg/ml to about 1 mg/ml. Furthermore, carvedilol presents low solubility in water, gastric fluid (simulated, TS, pH 1.1) and intestinal fluid (simulated, TS without pancreatin, pH 7.5). Carvedilol also presents a narrow absorption window. The relative absorption of carvedilol in the jejunum, ileum and colon is reported as 56%, 28% and 7% respectively. (See, e.g., WO2003/028718 and Nolte et al (Arzneimittelforschung 49(9):745-9, 1999)) Carvedilol's solubility and absorption limitations dictate immediate release commercial formulations for carvedilol that are administered twice a day. (See, e.g., Coreg® Prescribing Information)

Given the disadvantages and currently available carvedilol formulations, a need exists for a controlled release formulation of carvedilol that provides adequate bioavailability and extended release duration, allowing for a less frequent dosage requirement.

SUMMARY OF THE INVENTION

The present invention is a controlled release formulation of carvedilol with adequate bioavailability and extended release duration. The formulation comprises a therapeutically effective amount of carvedilol or a pharmaceutically acceptable salt thereof, a matrix forming polymer, a solubility enhancer, and a pharmaceutically acceptable carrier.

The invention further provides a controlled release formulation of carvedilol with two or more subunits, wherein at least one subunit comprises a therapeutically effective amount of carvedilol or a pharmaceutically acceptable salt thereof, a matrix forming polymer, a pharmaceutically acceptable carrier and wherein at least one subunit comprises a therapeutically effective amount of carvedilol or a pharmaceutically acceptable salt thereof, a matrix forming polymer, a solubility enhancer, and a pharmaceutically acceptable carrier.

Particularly, the present invention provides a controlled release formulation, comprising:
  (a) a therapeutically effective amount of carvedilol free base or carvedilol salt thereof;
  (b) a matrix forming polymer comprising one or more of the following: about 20% to about 60% by weight (e.g. about 25% to about 35% by weight) of Methocel K15M, about 15% to about 20% by weight of Methocel K100M, about 25% to about 35% by weight of Methocel E4M, about 35% to about 45% by weight of Eudragit RSPO, or about 35% to about 55% by weight of WSR N12NF;
  (c) a solubility enhancer comprising one or more of the following: about 25% to about 55% by weight of Povidone, about 25% to about 35% by weight of PEG6000, or about 35% to about 45% by weight of HPC-L; and
  (d) an excipient comprising one or more of the following: about 15% to about 35% by weight of corn starch, or about 0.1% to about 2% by weight of magnesium stearate.

The present invention also provides a controlled release formulation, comprising two or more subunits wherein at least one of said subunits is an immediate release carvedilol subunit comprising a therapeutically effective amount of carvedilol free base or carvedilol salt thereof, a matrix forming polymer, a solubility enhancer and a pharmaceutically acceptable carrier, and wherein at least one of said subunits is a slow release carvedilol subunit comprising a therapeutically effective amount of carvedilol free base or carvedilol salt thereof, a matrix forming polymer and a pharmaceutically acceptable carrier.

According to one embodiment of the present invention, the carvedilol is free base carvedilol.

According to one embodiment of the present invention, the matrix forming polymer comprises one or more of the following: hydroxypropyl methylcellulose (HPMC), polyoxethylene oxide, alginate, methylcellulose, ethycellulose, methacrylic copolymer, or hydroethylmethylcellulose (HEMC).

According to one embodiment of the present invention, the solubility enhancer comprises one or more of the following: hydroxypropyl cellulose (HPC), hydroxyethyl cellulose (HEC), polyvinylpyrrolidone (PVP), polyethylene glycol (PEG), or sodium lauryl sulfate (SLS).

According to one embodiment of the present invention, the pharmaceutically acceptable carrier comprises one or more of the following: lactose, corn starch or magnesium stearate.

The present invention further provides a controlled release formulation, comprising:
A. One or more immediate release subunits, comprising;
   (i) a therapeutically effective amount of carvedilol free base or carvedilol salt thereof;
   (ii) about 4% to about 5% by weight of a matrix forming polymer comprising one or more of the following: hydroxypropyl methylcellulose (HPMC), polyoxethylene oxide, alginate, methylcellulose, ethycellulose, a methacrylic copolymer, or hydroethylmethylcellulose (HEMC); and
   (iii) about 0.01% to about 0.1% by weight of an excipient; and
B. One or more slow release subunits, comprising;
   (i) a therapeutically effective amount of carvedilol free base or carvedilol salt thereof;
   (ii) about 20% to about 55% by weight of a matrix forming polymer comprising one or more of the following: hydroxypropyl methylcellulose (HPMC), polyoxethylene oxide, alginate, methylcellulose, ethycellulose, a methacrylic copolymer, or hydroethylmethylcellulose (HEMC);
   (iii) about 1.0% to about 30% by weight of a solubility enhancer comprising one or more of the following: hydroxypropyl cellulose (HPC), hydroxyethyl cellulose (HEC), polyvinylpyrrolidone (PVP), polyethylene glycol (PEG), or sodium lauryl sulfate (SLS); and
   (iv) about 0.01% to about 25% by weight of an excipient.

According to one embodiment of the present invention, the ethycellulose contains about 20% to about 80% (w/w) of ethoxyl.

According to one embodiment of the present invention, the methoxyl content of the hydroethylmethylcelluose (HEMC) is from about 10% to about 60% (w/w).

According to one embodiment of the present invention, the excipient comprises one or more of the following: lactose, corn starch or magnesium stearate.

According to one embodiment of the present invention, the controlled release formulation exhibits a ratio of a geometric mean of logarithmic transformed AUC0-∞ of the controlled release formulation to a geometric mean of logarithmic transformed AUC0-∞ of the reference drug (Coreg CR™) of about 0.80 to about 1.20; or the controlled release formulation exhibits a ratio of a geometric mean of logarithmic transformed $AUC_{0-t}$ of the controlled release formulation to a geometric mean of logarithmic transformed $AUC_{0-t}$ of the reference drug (Coreg CR™) of about 0.80 to about 1.20; or the controlled release formulation exhibits a ratio of a geometric mean of logarithmic transformed $C_{max}$ of the controlled release formulation to a geometric mean of logarithmic transformed $C_{max}$ of the reference drug (Coreg CR™) of about 0.80 to about 1.20.

According to one embodiment of the present invention, the controlled release formulation exhibits a first peak plasma $T_{max1}$ of about 4 hours, and a second peak plasma $T_{max2}$ of about 24 hours after oral administration to a patient.

Further provided is a method of making a controlled release formulation, comprising:
A. Making an immediate release subunit, comprising the steps of:
   i. Mixing and blending a therapeutically effective amount of carvedilol, about 4% to about 5% by weight of a matrix-forming polymer to form a first mixture;
   ii. Granulating said first mixture into first granules; and
B. Making a slow release subunit, comprising the steps of:
   i. Mixing and blending a therapeutically effective amount of carvedilol, about 20% to about 55% by weight of a matrix-forming polymer to form a mixture;
   ii. Adding about 1.0% to about 30% by weight of a solubility enhancer to said mixture to form a second mixture;
   iii. Granulating said second mixture into said second granules; and
C. Adding about 0.01% to about 25% by weight of an excipient to said first and second granules, and compressing said first and second granules into a tablet.

According to one embodiment of the present invention, the step of granulating said first mixture further comprises heating said first mixture at a temperature about 50° C. to about 70° C. The step of granulating said first mixture can further comprises sieving said first mixture through a 20 mesh sieve According to one embodiment of the present invention, the step of granulating said second mixture further comprises heating said second mixture at a temperature about 50° C. to about 70° C. The step of granulating said second mixture can further comprises sieving said second mixture through a 20 mesh sieve.

DETAILED DESCRIPTION OF THE INVENTION

Figure 1:
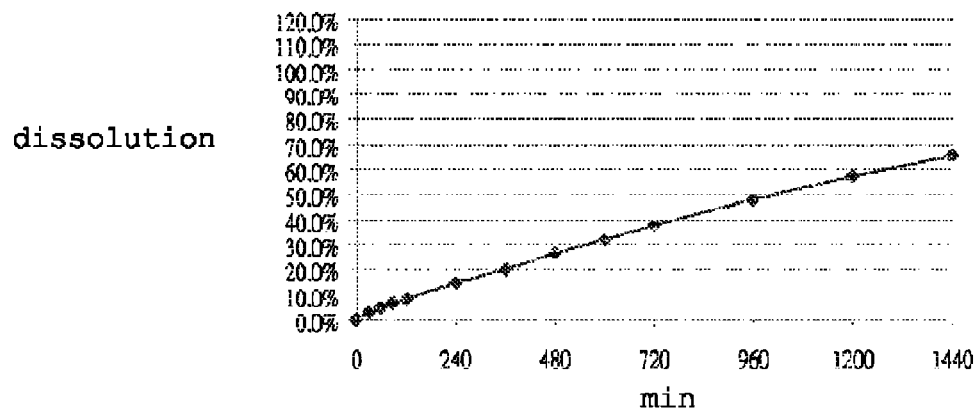
FIG. 1 shows the dissolution profile of the controlled release formulation in Table 1.
Figure 2:
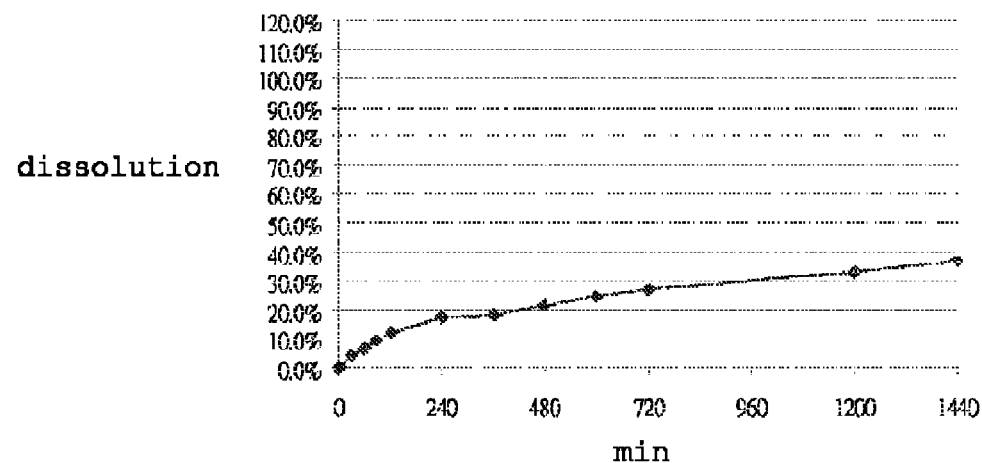
FIG. 2 shows the dissolution profile of the controlled release formulation in Table 2.
Figure 3:
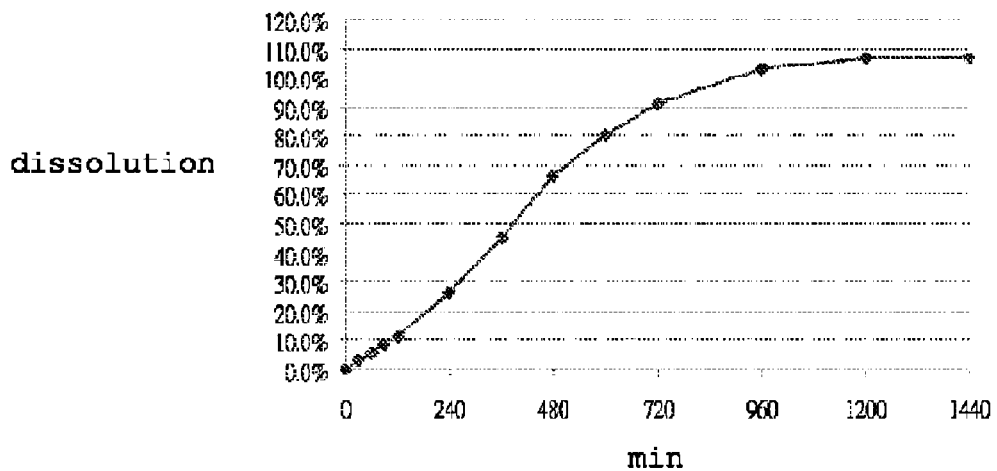
FIG. 3 shows the dissolution profile of the controlled release formulation in Table 3.
Figure 4:
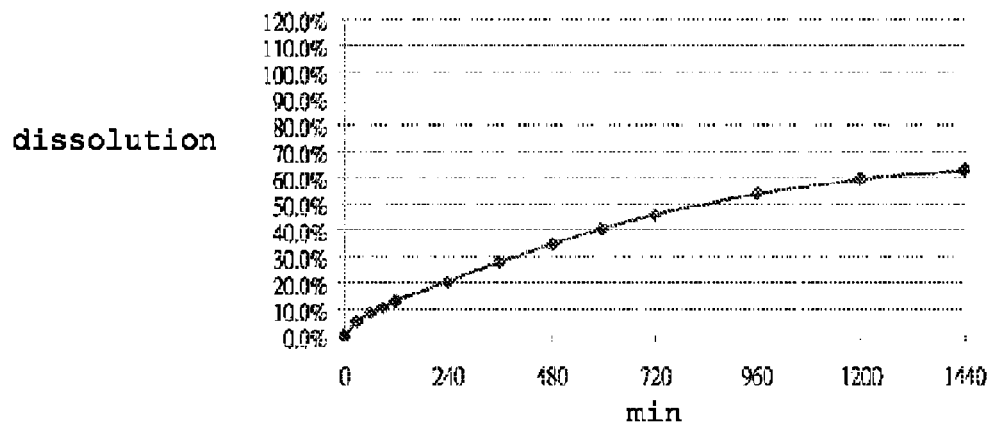
FIG. 4 shows the dissolution profile of the controlled release formulation in Table 4.
Figure 5:
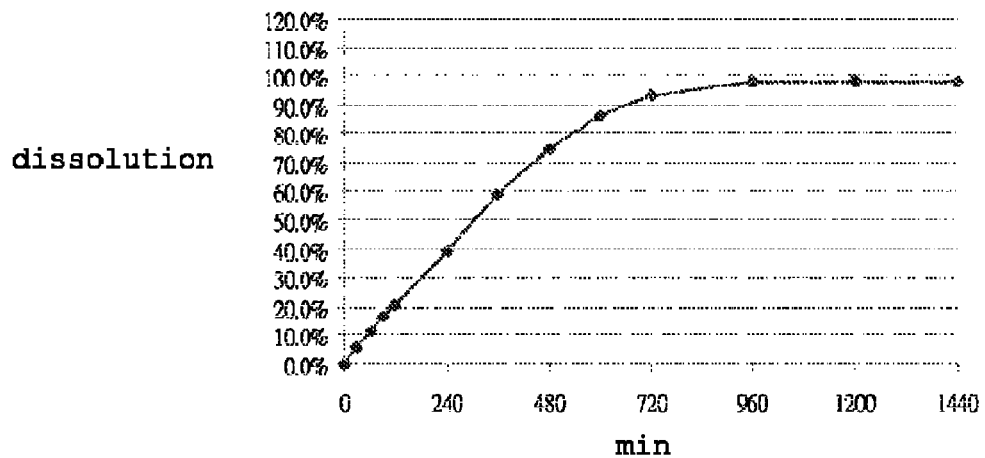
FIG. 5 shows the dissolution profile of the controlled release formulation in Table 5.
Figure 6:
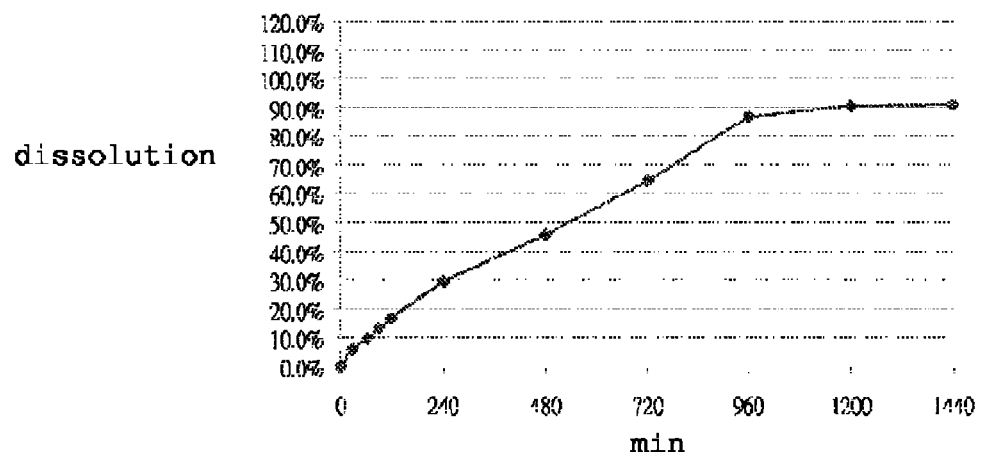
FIG. 6 shows the dissolution profile of the controlled release formulation in Table 6.
Figure 7:
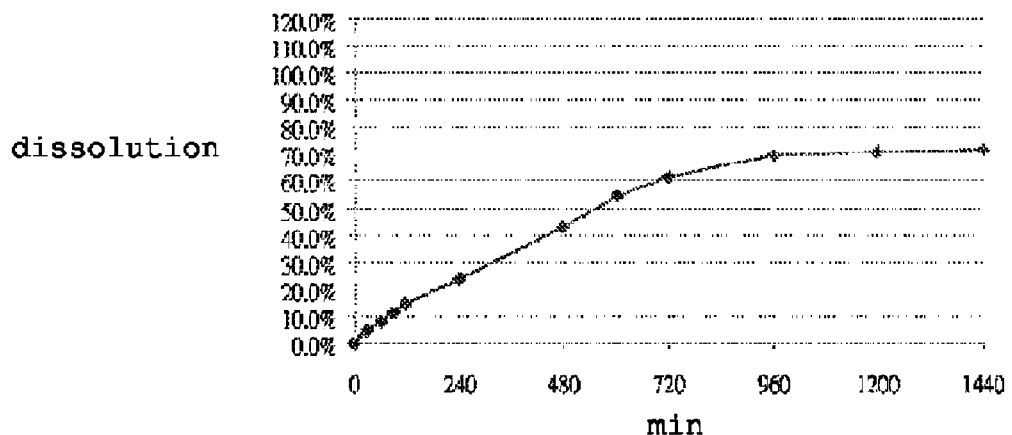
FIG. 7 shows the dissolution profile of the controlled release formulation in Table 7.

The present invention provides a controlled release carvedilol formulation, comprising a therapeutically effective amount of carvedilol or a pharmaceutically acceptable salt thereof, a matrix forming polymer, a solubility enhancer, and a pharmaceutically acceptable carrier.

In another aspect of the present invention, the controlled release formulation includes two or more subunits, wherein at least one subunit is an "immediate release" subunit and wherein at least one subunit is a "slow-release" subunit. The controlled release formulation delivers the desired pharmacokinetic profile by releasing carvedilol at different rates: a slow-release subunit that releases carvedilol slowly, and an immediate-release subunit that releases carvedilol more rapidly to provide a loading dose of carvedilol. One example of a subunit configuration includes: a single layered immediate release subunit combined with a single layered slow release subunit to form a bi-layered formulation. A second example is configured such that a slow release subunit forms the core and is surrounded by an immediate release subunit.

An "immediate-release subunit" comprises a therapeutically effective amount of carvedilol or a pharmaceutically acceptable salt thereof, a matrix forming polymer, and a pharmaceutically acceptable carrier. The immediate-release subunit releases carvedilol in a conventional or non-modified way, which is greater than or equal to about 60% of carvedilol released within two hours of administration, and generally within one hour of administration.

A "slow-release subunit" comprises a therapeutically effective amount of carvedilol or a pharmaceutically acceptable salt thereof, a matrix forming polymer, a solubility enhancer, and a pharmaceutically acceptable carrier. It releases carvedilol in a controlled or modified way over an extended period of time after administration, preferably over a period of about twenty-four hours. The solubility enhancer serves to increase the solubility of carvedilol in the proximal small intestine and extends the time of absorption.

A "subunit" includes a composition, mixture, particle, pellet, microcapsule, microtablet, or other pharmaceutically acceptable configuration that can deliver carvedilol alone or when combined with other subunits.

"The effective amount," as used herein, refers to an amount that alleviates or reduces one or more symptoms of cardiovascular diseases, such as high blood pressure, shortness of breath, and ankle swelling. The term "controlled release," as used herein, refers to the gradual release of carvedilol at a controlled rate over an extended period of time, preferably 24 hours, after the administration. The plasma concentration of carvedilol remains within the therapeutic range over an extended period of time, preferably 24 hours.

Carvedilol

The formulation of the present invention comprises a therapeutically effective amount of carvedilol, which can be prepared by known methods, for example, U.S. Pat. No. 4,503,067, which is incorporated herein by reference. In one embodiment, carvedilol is in the form of the free base.

"Pharmaceutically acceptable salts" include derivatives of carvedilol, wherein carvedilol is modified by making acidic salts thereof. Examples of pharmaceutically acceptable salts include, but are not limited to, salts of mineral or organic acids, for example, hydrochloric, hydrobromic, hydrofluoric, sulfuric, phosphoric, acetic, trifluoroacetic, benzoic, citric, maleic, succinic or methanesulfonic. Exemplary carvedilol salts include carvedilol benzoate, carvedilol citrate, carvedilol glutarate, carvedilol hydrobromide, carvedilol hydrochloride, carvedilol hydrogen phosphate, carvedilol dihydrogen phosphate, carvedilol lactate, carvedilol mandelate, carvedilol maleate, carvedilol mesylate, carvedilol oxalate, carvedilol sulfate, or a hydrate or solvate of the foregoing salts Carvedilol or a pharmaceutically acceptable salt thereof used in the present invention may be in crystalline, amorphous, polymorphic, anhydrous or hydrate form, or a combination of the forms thereof.

Matrix-Forming Polymer

The controlled release formulation is a matrix formulation in which the active compound is homogeneously dispersed in a matrix by using a matrix-forming polymer. The matrix-forming polymer as used in the invention comprises hydroxypropyl methylcellulose (HPMC), polyoxethylene oxide, alginate, methylcellulose, ethycellulose, a methacrylic copolymer, hydroethylmethylcellulose (NEMC), or any combination thereof.

In one embodiment, the HPMC has a molecular weight in the range from about 4,000 to about 220,000 Da. "About" as used herein, refers to ±15% of the recited value. A person skilled in the art will understand that different grades of HPMC can be used in the formulation according to the present invention. For example, Methocel™ E4M Premium 2, Methocel™ E10M Premium CR, METHOCEL™ F50 Premium, METHOCEL™ F4M Premium, METHOCEL™ K4M Premium2, METHOCEL™ K15M Premium2, and METHOCEL™ K100M 10 Premium2 (commercially available from Dow Chemical Company) can be used.

In another embodiment, the polyoxethylene oxide has a molecular weight in the range from about 100,000 to about 7,000,000 Da. A person skilled in the art will understand that different grades of polyoxethylene oxide can be used in the formulation according to the present invention. For example, Polyox™ WSR N-10 NF, 15 Polyox™ WSR N-12 NF, Polyox™ WSR N-80 NF, Polyox™ WSR N-750 NF, Polyox™ WSR-205 NF, Polyox™ WSR-1105 NF, Polyox™ WSR N-12K NF, Polyox™ WSR N-60K NF, PolyoxT™ WSR-301 NF, Polyox™ WSR Coagulant NF, and Polyox™ WSR-303 NF (commercially available from Dow Chemical Company) can be used.

In another embodiment, the alginate has a molecular weight in the range from about 10,000 to about 50,000 Da. A person skilled in the art will understand that different grades of alginate can be used in the formulation according to the present invention.

In one embodiment of the invention, the methylcellulose has a molecular weight in the range from about 10,000 to about 250,000 Da. A person skilled in the art will understand that different grades of methylcellulose can be used in the formulation according to the present invention. Examples of methylcellulose include METHOCEL™ A15 Premium LV, METHOCEL™ A4C Premium, METHOCEL™ A15C Premium, and METHOCEL™ A4M Premium (commercially available from Dow Chemical Company).

In yet another embodiment, the ethycellulose contains about 20% to about 80% (w/w) of ethoxyl, preferably about 45% to 55% (w/w). Examples of ethycellulose include ETHOCEL Standard 4 Premium, ETHOCEL Standard 7 Premium, ETHOCEL Standard 10 Premium, ETHOCEL Standard 14 Premium, ETHOCEL Standard 20 Premium, ETHOCEL Standard 45 Premium, and ETHOCEL Standard 100 Premium (commercially available from Dow Chemical Company).

In another embodiment, the methacrylic copolymer has a molecular weight in the range from about 10,000 to about 1,500,000 Da. Examples, of methacrylic copolymer include EUDRAGIT® L, EUDRAGIT® S 100, EUDRAGIT® E 100, EUDRAGIT® E PO, EUDRAGIT® E 12.5, EUDRAGIT® L 100-55, EUDRAGIT® L 30 D-55, EUDRAGIT® NE 30 D, EUDRAGIT® RL 100, EUDRAGIT® RS 100, 10 EUDRAGIT® RL PO, EUDRAGIT® RS PO, EUDRAGIT® RL 12.5, EUDRAGIT® RS 12.5, EUDRAGIT® RL 30 D, EUDRAGIT® RS 30 D, EUDRAGIT® NM 30 D, and EUDRAGIT® FS 30 D (commercially available from Evonik Industries AG).

In another embodiment, the HEMC contains about 10 to about 60% (w/w) of methoxy content, preferably about 15% to about 45% (w/w). Example of HEMC includes CULMINAL®, which is commercially available from Ashland Inc.

Solubility Enhancer

The solubility enhancer of the present invention comprises of hydroxypropyl cellulose (HPC), hydroxyethyl cellulose (HEC), polyvinylpyrrolidone (PVP), polyethylene glycol (PEG), sodiumlauryl sulfate (SLS), or any combination thereof.

In one embodiment, the HPC has a molecular weight of about 50,000 to about 1,250,000 Da. Examples of HPC include HPC-L, HPC-M, and HPC-SL (commercially available from Nisso America Inc.).

In one embodiment, the HEC has a molecular weight of about 80,000 to about 1,500,000 Da. Examples of HEC include Natrosol®, which is commercially available from Ashland Inc.

In another embodiment, the PVP has a molecular weight from about 2,500 to about 3,000,000 Da. Examples of PVP includes Kollidon®, which is commercially available from BASF.

In yet another embodiment, the PEG has a molecular weight from about 200 to about 35,000 Da. Examples of PEG include PEG200, PEG400, PEG600, PEG1000, PEG2000, PEG3000, PEG4000, PEG6000, and PEG8000.

Pharmaceutically Acceptable Carrier

In one embodiment of the invention, a "pharmaceutically acceptable carrier" refers to a carrier that, after administration to or upon a subject, does not cause undesirable physiological effects. The carrier in a pharmaceutical composition must be "acceptable" also in the sense that it is compatible with the active ingredient and, preferably, capable of stabilizing it. One or more solubilizing agents can be used as pharmaceutical carriers for delivery of carvedilol. Pharmaceutically acceptable carriers can be selected by those skilled in the art using conventional criteria. Pharmaceutically acceptable carriers include, but are not limited to, sterile water or saline solution, aqueous electrolyte solutions, isotonicity modifiers, water polyethers such as polyethylene glycol, polyvinyls such as polyvinyl alcohol and povidone, cellulose derivatives such as methylcellulose and hydroxypropyl methylcellulose, polymers of acrylic acid such as carboxypolymethylene gel, polysaccharides such as dextrans, and glycosaminoglycans such as sodium hyaluronate and salts such as sodium chloride and potassium chloride.

In another embodiment of the invention, a pharmaceutically acceptable carrier refers to one or more excipients that are normally employed in the oral formulations, such as fillers, extenders, binders, humectants, disintegrating agents, wetting agents, and/or lubricants. Examples of the excipients used in the invention include, but are not limited to cellulose, microcrystalline, starch, corn starch, lactose, sucrose, glucose, mannitol, silicic acid, citric acid, crospovidone, sodium chloride, cetyl alcohol, glycerol monostearate, kaolin, bentonite clay, talc, calcium stearate, magnesium stearate, and solid polyethylene glycols.

Formulation

In the present invention, carvedilol is present in an amount of about 1% to about 40% by weight of the formulation, and preferably about 9% to about 25%, and more preferably about 9.5% to 10.5%. The matrix-forming polymer is present in an amount of about 10% to about 80% by weight of the formulation, and preferably about 2% to about 55%, and more preferably about 35% to 45%. The solubility enhancer is present in an amount of about 0.1% to about 60% by weight of the formulation, and preferably about 1.5% to 55%, and more preferably about 15% to 25%. The excipient is present in an amount of about 0.1% to about 75% by weight of the formulation, and preferably about 0.3% to about 35%.

In one embodiment, the controlled release formulation comprises a combination of about 15% to about 35% of HPMC and about 20% to about 55% of PVP. In another embodiment, the controlled release formulation comprises a combination of about 25% to about 35% of HPMC and about 25% to about 35% of PEG. In another embodiment, the controlled release formulation comprises a combination of about 35% to about 45% of Eudragit and about 35% to about 45% of HPC. In another embodiment, the controlled release formulation comprises a combination of about 40% to about 50% of polyoxyethylene oxide and about 25% to about 35% of PVP. In yet another embodiment, the controlled release formulation comprises a combination of about 35% to about 45% of polyoxyethylene oxide and about 35% to about 45% of HPC.

The pharmaceutical composition of the present invention may be constituted into any form suitable for the mode of administration selected. For example, compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The controlled release formulation of carvedilol can be prepared using any conventional methods such as dry granulation or wet granulation followed by compression or compaction. For example, the most common method of preparation involves mixing carvedilol with a matrix-forming polymer and the solubility enhancer, followed by granulating the mixture, sieving the granules formed through a 10 to 40 (preferably 20 to 30) mesh sieve, heating the granules at about 50° C. to about 70° C. (preferably at about 60° C.) and compressing the granules into tablets. Details for the preparation are described in the following examples.

Dissolution

A dissolution profile is a plot of the cumulative amount of active agent released as a function of time. A dissolution profile can be measured utilizing the Drug Release Test <724>, which incorporates standard test USP 26 (Test <711>). A profile is characterized by the test conditions selected such as, for example, apparatus type, shaft speed, temperature, volume, and pH of the dissolution medium. More than one dissolution profile can be measured. For example, a first dissolution profile can be measured at a pH level approximating that of stomach, and a second dissolution profile can be measured at a pH level approximating that of one point in the intestine or several pH levels approximating multiple points in the intestine.

A highly acidic pH may be employed to simulate the stomach and a less acidic to basic pH may be employed to simulate the intestine. By the term "highly acidic pH" is meant a pH of about 1 to about 4.5. A pH of about 1.2, for example, can be used to simulate the pH of stomach. By the term "less acidic to basic pH" is meant a pH of greater than about 4 to about 7.5, specifically about 6 to about 7.5. A pH of about 6 to about 7.5, specifically about 6.8, can be used to simulate the pH of the intestine.

Pharmacokinetic Study

Bioequivalence of carvedilol composition to a reference drug can be determined by an in vivo bioequivalence study to determine a pharmacokinetic parameter for the carvedilol composition. Specifically, bioequivalence can be determined by an in vivo bioequivalence study comparing a pharmacokinetic parameter for the two compositions. A pharmacokinetic parameter for the carvedilol composition or the reference drug can be measured in a single or multiple dose bioequivalence study using a replicate or a nonreplicate design. Single doses of the test composition and reference drug are administered and blood or plasma levels of the active agent are measured over time. Pharmacokinetic parameters characterizing rate and extent of active agent absorption are evaluated statistically.

The area under the plasma concentration-time curve from time zero to the time of measurement of the last quantifiable concentration ($AUC_{0-t}$) and to infinity ($AUC_{0-\infty}$), $C_{max}$, and $T_{max}$ can be determined according to standard techniques. Statistical analysis of pharmacokinetic data is performed on logarithmic transformed data (e.g., $AUC_{0-t}$, $AUC_{0-\infty}$, or $C_{max}$ data) using analysis of variance (ANOVA).

In other embodiments, the single dose pharmacokinetic study is conducted between the controlled-release carvedilol composition and the reference listed drug using the strength specified by the FDA in APPROVE DRUG PRODUCTS WITH THERAPEUTIC EQUIVALENCE EVALUATIONS (ORANGE BOOK).

Under U.S. FDA guidelines, two products (e.g. an inventive composition and COREG CR™) are bioequivalent if the 90% Confidence Interval (CI) limits for a ratio of geometric mean of logarithmic transformed $AUC_{0-t}$, $AUC_{0-\infty}$, and $C_{max}$ for the two products are about 0.80 to about 1.25.

In one embodiment, in a given experiment, a carvedilol composition is considered to be bioequivalent to COREG CR™ if both the Test/Reference ratio for the geometric mean of logarithmic transformed $AUC_{0-t}$, $AUC_{0-\infty}$, or $C_{max}$ ratio along with its corresponding lower and upper 90% CI limits are within a lower limit of about 0.80 and an upper limit of about 1.25. Thus, for direct comparison between a carvedilol composition and Coreg CR™, it is sometimes preferred to determine the pharmacokinetic parameters for the carvedilol composition and Coreg CR™ side-by side in the same pharmacokinetic study.

The controlled release formulation of the invention allows the release of carvedilol to be extended over at least 6 hours, and preferably at least 12 hours, and more preferably at least 24 hours, after administration even when the surrounding pH turns neutral (i.e. during passage through the small intestine in vivo).

Accordingly, the present invention further provides a method of delivering carvedilol to a subject in need thereof which comprises administering to the subject a controlled release carvedilol formulation, comprising one or more subunits disclosed and described herein.

The method of the invention is useful for the treatment of cardiovascular disorders, such as hypertension, angina, congestive heart failure, and left ventricular dysfunction following myocardial infarction.

The following examples further illustrate the present invention. These examples are intended merely to be illustrative of the present invention and are not to be construed as being limiting.

EXAMPLE

Example 1

Preparation of Carvedilol Controlled Release Formulation

The controlled release formulation of the present invention was prepared by wet granulations followed by compression, as illustrated below:

1. The exact amount of carvedilol and other ingredients (including a matrix-forming polymer and a solubility enhancer) were weighed, except for magnesium stearate, and then transferred to a high shear granulation machine;
2. The ingredients in Step 1 were added to the blender and blended for 3 minutes with the appropriate impeller and chopper speed to form a mixture;
3. The mixture in Step 2 was dispersed in ethanol and water to start the granulation process;
4. The impeller and chopper settings and the characteristics of the granulation solution were monitored;
5. The granulation solution in Step 4 was granulated using a granulate machine and screened through a 20 to 30 mesh sieve when the granulation end-point was reached;
6. The granules in Step 5 were heated in an oven at 60° C. and the moisture content of the granules was maintained at a range between 1.0% to 3.0%;
7. An exact amount of magnesium stearate was weighed and mixed with the granules in Step 6;
8. The sample in Step 7 was compressed by a high speed rotary tabletting machine to form tablets.

Tables 1 to 7 show the contents of the controlled release formulation prepared in according to the steps described above.

TABLE 1

| Ingredient | Weight (mg) | % |
| --- | --- | --- |
| Carvedilol | 63.46 | 12.69% |
| HPMC (Methocel K15M) | 145.00 | 29.00% |
| Corn Starch | 145.00 | 29.00% |
| Povidone (Kollidon ®) | 145.00 | 29.00% |
| Magnesium Stearate | 1.50 | 0.30% |
| Total | 499.96 | 100.00% |

TABLE 2

| Ingredient | Weight (mg) | % |
| --- | --- | --- |
| Carvedilol | 63.46 | 12.69% |
| HPMC (Methocel K15M) | 155.00 | 31.00% |
| Corn Starch | 155.02 | 31.01% |
| Povidone (Kollidon ®) | 125.00 | 25.00% |
| Magnesium Stearate | 1.50 | 0.30% |
| Total | 499.98 | 100.00% |

TABLE 3

| Ingredient | Weight (mg) | % |
| --- | --- | --- |
| Carvedilol | 63.46 | 12.69% |
| HPMC (Methocel K100M) | 87.00 | 17.40% |
| Corn Starch | 87.00 | 17.40% |
| Povidone (Kollidon ®) | 261.00 | 52.20% |
| Magnesium Stearate | 1.50 | 0.30% |
| Total | 499.96 | 100.00% |

TABLE 4

| Ingredient | Weight (mg) | % |
| --- | --- | --- |
| Carvedilol | 63.46 | 12.69% |
| HPMC (Methocel E4M) | 145.00 | 29.00% |
| Corn Starch | 145.00 | 29.00% |

TABLE 4-continued

| Ingredient | Weight (mg) | % |
|---|---|---|
| PEG 6000 | 145.00 | 29.00% |
| Magnesium Stearate | 1.50 | 0.30% |
| Total | 499.96 | 100.00% |

TABLE 5

| Ingredient | Weight (mg) | % |
|---|---|---|
| Carvedilol | 63.30 | 21.10% |
| Eudragit RSPO | 117.60 | 39.20% |
| HPC-L | 117.60 | 39.20% |
| Magnesium Stearate | 1.50 | 0.50% |
| Total | 300.00 | 100.00% |

TABLE 6

| Ingredient | Weight (mg) | % |
|---|---|---|
| Carvedilol | 63.30 | 21.10% |
| Polyox (WSR N12 NF) | 141.12 | 47.04% |
| Povidone (Kollidon ®) | 94.08 | 31.36% |
| Magnesium Stearate | 1.50 | 0.50% |
| Total | 300 | 100.00% |

TABLE 7

| Ingredient | Weight (mg) | % |
|---|---|---|
| Carvedilol | 63.30 | 21.10% |
| Polyox (WSR N12 NF) | 117.60 | 39.20% |
| HPC-L | 117.60 | 39.20% |
| Magnesium Stearate | 1.50 | 0.50% |
| Total | 300.00 | 100.00% |

Example 2

Dissolution Test of Carvedilol Controlled Release Formulation

Dissolution was performed in accordance with the United States Pharmacopeia (USP 31-NF 26) 711, Dissolution, Apparatus II. Hydrochloric acid (0.1N) was used as the dissolution medium during the first 120 min. The pH of the dissolution medium was changed to pH 4.5 by adding a phosphate buffer. At 240 minutes, the dissolution medium was further changed to a pH of 6.8 by adding a phosphate buffer. Dissolution was performed in 900 ml dissolution medium with a paddle speed of 100 rpm over 24 hours. Samples were taken at suitable time intervals and analyzed for carvedilol content by means of high-pressure liquid chromatography (HPLC). FIGS. 1 to 7 show the dissolution profiles of Table 1 to Table 7 Formulations, respectively. These results show that the controlled release formulation prepared in accordance with Tables 1 to 7 extends the duration of release and maintains adequate dissolution for at least 24 hours.

Example 3

Preparation of the Controlled Release Formulation (T1 Formulation)

Immediate-Release Subunit

Immediate-release subunits were prepared by a granulation process followed by compression into compressed subunits, as illustrated below:

1. 76.25 Grams of carvedilol, 296.25 grams of Flow Lac 100 (Lactose) and 125.60 grams of Methocel K100LV were weighed and blended for 5 minutes;
2. The mixture in Step 1 was screened through a 40 mesh sieve, and blended for another 10 minutes;
3. The mixture in Step 2 was transferred to a high shear granulator and mixed for 1 minute;
4. The mixture in Step 3 was dispersed in 200 ml of 95% ethanol and 55 ml of water to start the granulation process;
5. The granules in Step 4 were heated in an oven at 60° C. for 8 hours, and the moisture content of the granules was maintained at a range between 1.0% to 3.0%;
6. The granulation solution was further screened through a 20 mesh sieve;
7. 1.5 Grams of magnesium stearate was added to said immediate release granules in the first cell of a rotatory double-deck tabletting machine.

Slow-Release Subunit

Slow-release subunits were prepared by a granulation process followed by compression into compressed subunits, as illustrated below:

1A. 240.0 Grams of carvedilol, 600 grams of corn starch and 600 grams of Methocel K15M were weighed and blended for 5 minutes;

2A The mixture in Step 1A was screened through a 40 mesh sieve, and blended for another 10 minutes;

3A. The mixture in step 2A was transferred to a to a high shear granulation machine and mixed for 1 minute;

4A. The mixture in Step 3A was dispersed in 638.5 ml of 95% ethanol and mixed for 5 minutes;

5A. 187.5 Grams of Povidone K30 was added and mixed for 1 minute, a further 250 grams of Povidone K30 was added and mixed for 1 minute, and another 250 grams of Povidone K30 was added and mixed for 3 minutes.

6A. The granules in Step 5A were heated in an oven at 60° C. for 8 hours, and the moisture content of the granules was maintained at a range between 1.0% to 3.0%;

7A. The granulation solution was further screened through a 20 mesh sieve;

8A. 6.0 Grams of magnesium stearate was added to said slow release granules in the second cell of a rotatory double-deck tabletting machine.

Formation of Controlled Release Formulation

The bi-layered controlled release formulation was formed by compressing the slow release granules in Step 8A and immediate release granules in Step 7 in the rotating double-deck tabletting machine. The resulting controlled release carvedilol formulation contained a total of about 63.46 mg of carvedilol. Table 8 shows the ingredients of the controlled release formulation (T1 formulation), manufactured by the process described above.

TABLE 8

| Ingredient | Weight (mg) | |
|---|---|---|
| Immediate-Release Subunit: | | |
| Carvedilol | 15.46 | 2.9% |
| HPMC(Methocel K100LV) | 25.04 | 4.8% |
| Lactose | 59.20 | 11.3% |
| Magnesium Stearate | 0.30 | 0.0% |
| Slow-Release Subunit: | | |
| Carvedilol | 48.00 | 9.1% |
| HPMC (Methocel K15M) | 120.00 | 22.8% |
| Corn starch | 120.00 | 22.8% |
| PVP | 137.50 | 26.2% |
| Magnesium Stearate | 1.20 | 0.0% |
| Total | 526.7 | |

Example 4

Preparation of the Controlled Release Formulation (T2 Formulation)

Immediate-Release Subunit

Immediate-release subunits were prepared by a granulation process followed by compression into compressed subunits, as illustrated below:
1. 76.25 Grams of carvedilol, 296.25 grams of Flow Lac 100 (Lactose) and 125.60 grams of Methocel K100LV were weighed and blended for 5 minutes
2. The mixture in Step 1 was screened through a 40 mesh sieve, and blended for another 10 minutes;
3. The mixture in Step 2 was transferred to a high shear granulation machine and mixed for 1 minute;
4. The mixture in Step 3 was dispersed in 200 ml of 95% ethanol and 55 ml of water to start the granulation process;
5. The granules in Step 4 were heated in an oven at 60° C. for 8 hours, and the moisture content of the granules was maintained at a range between 1.0% to 3.0%;
6. The granulation solution was further screened through a 20 mesh sieve;
7. 1.5 Grams of magnesium stearate was added to said immediate release granules in the first cell of a rotary double-deck tabletting machine.

Slow-Release Subunit

Slow-release subunits were prepared by a granulation process followed by compression into compressed subunits, as illustrated below:
1A. 240.0 Grams of carvedilol, 500 grams of corn starch, 1500 grams of Methocel K15M and 50 grams of Sodium Lauryl Sulfate were weighed and the mixture was blended for 5 minutes;
2A. The mixture in Step 1A was screened through a 40 mesh sieve, and blended for another 10 minutes;
3A. The mixture in Step 2A was transferred to a to a high shear granulator and mixed for 1 minute;
4A. The mixture in Step 3A was dispersed in 1374 ml of 95% ethanol and 1832 ml of water and mixed for 3 minutes;
5A. The granules in Step 4A were heated in an oven at 60° C. for 8 hours, and the moisture content of the granules was maintained at a range between 1.0% to 3.0%;
6A. The granulation solution was further screened through a 20 mesh seive;
7A. 6.0 Grams of magnesium stearate was added to said slow release granules in the second cell of a rotatory double-deck tabletting machine.

Formation of Controlled Release Formulation

The bi-layered controlled release formulation was formed by compressing the slow release granules in Step 7A and immediate release granules in Step 7 in the rotating double-deck tabletting machine. The resulting controlled release carvedilol formulation contained a total of about 63.46 mg of carvedilol. Table 9 shows the ingredients of the controlled release formulation (T2 formulation) manufactured by the above process.

TABLE 9

| Ingredient | Weight (mg) | |
|---|---|---|
| Immediate-Release Subunit: | | |
| Carvedilol | 15.46 | 2.7% |
| HPMC(K100LV) | 25.04 | 4.5% |
| Lactose | 59.20 | 10.6% |
| Magnesium Stearate | 0.30 | 0.0% |
| Slow-Release Subunit: | | |
| Carvedilol | 48.00 | 8.6% |
| HPMC (Methocel K15M) | 300.00 | 53.6% |
| Corn starch | 100.00 | 17.9% |
| Sodium lauryl sulfate | 10.00 | 1.8% |
| Magnesium Stearate | 1.20 | 0.0% |
| Total | 559.2 | |

Example 5

Dissolution Test of Carvedilol Controlled Release Formulation (T1/T2 Formulations)

Dissolution was performed in accordance with the United States Pharmacopeia (USP 31-NF 26) 711, Dissolution, Apparatus II. Hydrochloric acid (0.1N) was used as the dissolution medium during the first 120 min. The pH of the dissolution medium was changed to pH 4.5 by adding a phosphate buffer. At 240 minutes, the dissolution medium was further changed to a pH of 6.8 by adding a phosphate buffer. Dissolution was performed in 900 ml dissolution medium with a paddle speed of 100 rpm over 24 hours. Samples were taken at suitable time intervals and analyzed for carvedilol content by means of high pressure liquid chromatography (HPLC).

Figure 8:
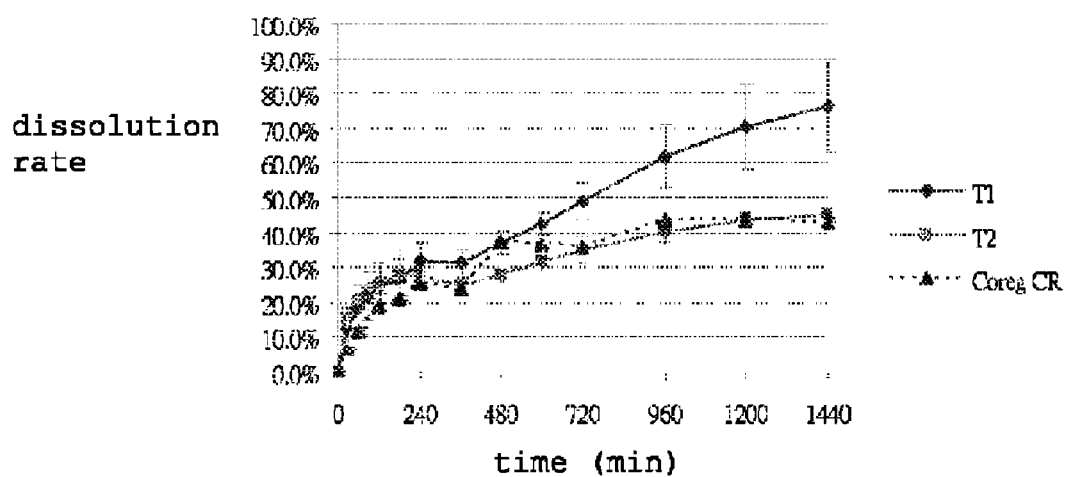
FIG. 8 shows the dissolution profile of the T1 and T2 formulations in Tables 8 and 9, respectively.

FIG. 8 shows the dissolution profiles of T1/T2 Formulations and reference drug, Coreg CR™ (commercially available from GSK). The result shows that the controlled release formulations prepared in accordance with Tables 8 and 9 extends the duration of release and maintains adequate dissolution for at least 24 hours.

Example 6

Preparation of the Controlled Release Formulation (T4 Formulation)

Immediate-Release Subunit

Immediate-release subunits were prepared by a granulation process followed by compression into compressed subunits, as illustrated below:
1. 4 Grams of carvedilol, 32.5 grams of Granulac 200 and 13.5 grams of Methocel K100LV were weighed and blended for 5 minutes;
2. The ingredients in Step 1 were transferred to a high shear granulation machine and mixed for 1 minute;

3. The mixture in Step 2 in was dispersed in 20 ml of 95% ethanol and 5.5 ml of water to start the granulation process;
4. The granules in Step 3 were heated in an oven at 60° C. for 8 hours, and the moisture content of the granules was maintained at a range between 1.0% to 3.0%;
5. The granulation solution was screened through a 20 mesh sieve;
6. 0.15 Gram of magnesium stearate was added to said immediate release granules in the first cell of a rotatory double-deck tabletting machine.

Slow-Release Subunit

Slow-release subunits were prepared by a granulation process followed by compression into compressed subunits, as illustrated below:

1A. 27.7 Grams of carvedilol, 60 grams of corn starch and 115 grams of Methocel K15M were weighed and blended for 5 minutes;
2A. The mixture in Step 1A was transferred to a high shear granulation machine and mixed for 1 minute;
3A. The mixture in Step 2A was dispersed in 63.9 ml of 95% ethanol and mixed for 5 minutes;
4A. 18.8 Grams of Povidone K30 was added and mixed for 1 minute, a further 15.0 grams of Povidone K30 was added and mixed for 1 minute, and another 15.0 grams of Povidone K30 was added and mixed for 3 minutes.
5A. The granules in Step 4A were heated in an oven at 60° C. for 8 hours, and the moisture content of the granules was maintained at a range between 1.0% to 3.0%;
6A. The granulation solution was screened through a 20 mesh sieve;
7A. 0.8 Gram of magnesium stearate was added to said slow release granules in the second cell of a rotatory double-deck tabletting machine.

Formation of Controlled Release Formulation

The bi-layered controlled release formulation was formed by compressing the slow release granules in Step 7A and immediate release granules in Step 6 in the rotating double-deck tabletting machine. The resulting controlled release carvedilol formulation contained a total of about 63.3 mg of carvedilol. Table 10 shows the ingredients of the controlled release formulation (T4 formulation), manufactured by the process described above.

TABLE 10

| Ingredient | Weight (mg) | |
| --- | --- | --- |
| Immediate-Release Subunit: | | |
| Carvedilol | 8.0 | 1.2% |
| Granulac 200 (Lactose) | 65.0 | 10.1% |
| Methocel (K100LV) | 27.0 | 4.2% |
| Magnesium Stearate | 0.30 | 0.0% |
| Slow-Release Subunit: | | |
| Carvedilol | 55.3 | 8.6% |
| Corn starch | 120.0 | 18.6% |
| Methocel K15M | 230.0 | 35.7% |

TABLE 10-continued

| Ingredient | Weight (mg) | |
| --- | --- | --- |
| Povidone K30 | 137.5 | 21.3% |
| Magnesium Stearate | 1.6 | 0.2% |
| Total | 644.70 | |

Example 7

Dissolution Test of Carvedilol Controlled Release Formulation (T4 Formulation)

Dissolution was performed in accordance with the United States Pharmacopeia (USP 31-NF 26) 711, Dissolution, Apparatus II. Hydrochloric acid (0.1N) was used as the dissolution medium during the first 120 min. The pH of the dissolution medium was changed to pH 4.5 by adding a phosphate buffer. At 240 minutes, the dissolution medium was further changed to a pH of 6.8 by adding a phosphate buffer. Dissolution was performed in 900 ml dissolution medium with a paddle speed of 100 rpm over 24 hours. Samples were taken at suitable time intervals and analyzed for carvedilol content by means of high pressure liquid chromatography (HPLC).

Figure 9:
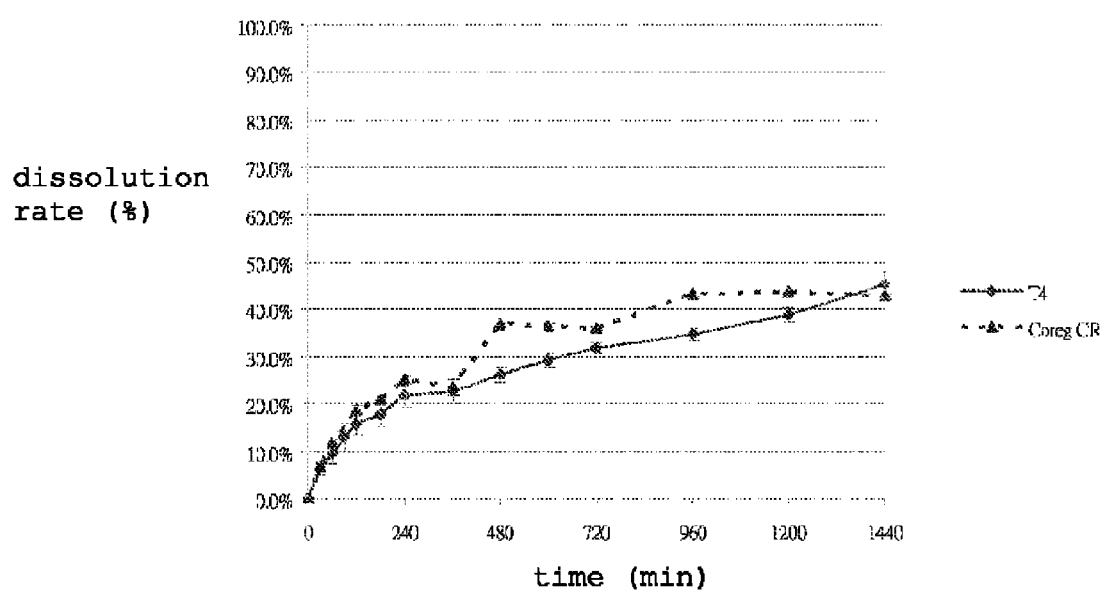
FIG. 9 shows the dissolution profile of the T4 formulation in Table 10.

FIG. 9 shows the dissolution profile of T4 Formulation and reference Drug (Coreg CR™). The result shows that the controlled release formulation prepared in accordance with Table 10 extends the duration of release and maintains adequate dissolution for at least 24 hours.

Example 8

PK Data of the T4 Formulation

An open-label, two-way, crossover study of the T4 Formulation versus Coreg CR™ was performed in normal healthy subjects. This study addresses the bioequivalence of carvedilol from the T4 Formulation under relevant clinical conditions.

Study Design:

Twelve healthy subjects with stable vital signs, a body weight above 50 kg and ability to communicate with the investigators were included in this study. The two dosing periods were separated by a washout period of at least three days. The two dosing regimens were as follows: 25 mg of T4 Formulation and 25 mg of Coreg CR™, administered 30 minutes after the initiation of a standardized breakfast preceded by an overnight fasting. Blood samples were taken 30 minutes before dosing (0 h) and 1.5, 3, 4, 5, 6, 7, 8, 10, 12, 14, 16 and 24 hours post dose for the T4 formulation and Coreg CR™.

Results:

Table 11 summarizes the mean pharmacokinetic parameters of carvedilol after subjects received Coreg CR™ (Reference drug) and T4 formulation.

TABLE 11

| Parameters | $AUC_{0-t}$ (ng/mL × hr) | $AUC_{0-\infty}$ (ng/mL × hr) | $AUC_{0-t}/AUC_{0-\infty}$ | $C_{max}$ (ng/mL) | $T_{max}$ (hr) | MRT (hr) | $T_{1/2}$ (hr) | RSQ |
| --- | --- | --- | --- | --- | --- | --- | --- | --- |
| Reference drug | | | | | | | | |
| Mean | 864.4 | 976.3 | 89.7 | 115.229 | 6.83 | 12.34 | 7.25 | 0.9730 |
| SD | 501.7 | 596.8 | 4.2 | 44.350 | 3.54 | 2.43 | 2.33 | 0.0176 |
| CV (%) | 58.0 | 61.1 | 4.7 | 38.5 | 51.8 | 19.7 | 32.2 | 1.8 |

TABLE 11-continued

| Parameters | $AUC_{0-t}$ (ng/mL × hr) | $AUC_{0-\infty}$ (ng/mL × hr) | $AUC_{0-t}/AUC_{0-\infty}$ | $C_{max}$ (ng/mL) | $T_{max}$ (hr) | MRT (hr) | $T_{1/2}$ (hr) | RSQ |
|---|---|---|---|---|---|---|---|---|
| Test drug (T4) | | | | | | | | |
| Mean | 779.4 | 950.0 | 83.7 | 116.783 | 5.21 | 14.98 | 10.98 | 0.9638 |
| SD | 452.6 | 527.2 | 14.0 | 93.013 | 3.88 | 8.60 | 7.30 | 0.0562 |
| CV (%) | 58.1 | 55.5 | 16.8 | 79.6 | 74.4 | 57.4 | 67.0 | 5.8 |

Table 12 shows a summary of pharmacokinetic ratio of Coreg™ (Reference drug) and T4 Formulation.

TABLE 12

| | PK Value | | |
|---|---|---|---|
| Comparison | $AUC_{0-t}$ Ratio | $AUC_{0-\infty}$ Ratio | $C_{max}$ Ratio |
| T4/R Geometric Mean ratio | 0.8962 | 0.9749 | 0.8632 |
| T4/R Mean ratio | 0.9017 | 0.9730 | 1.0135 |

Figure 10A:
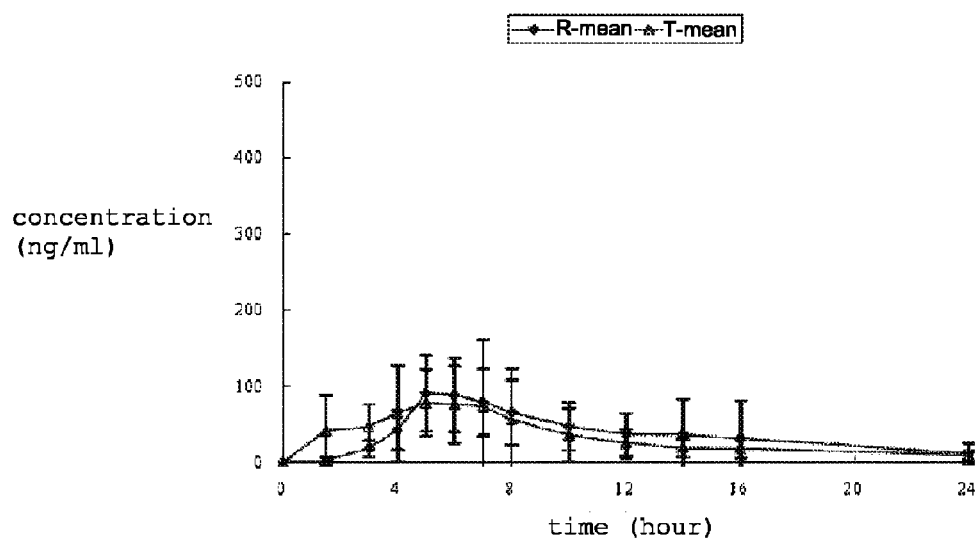
FIG. 10(A) shows the mean plasma concentration-time profile of carvedilol with the Linear ordinate after subjects received the reference drug (Coreg CR™) (●R-Mean) and the T4 formulation (ΔT-Mean)
Figure 10B:
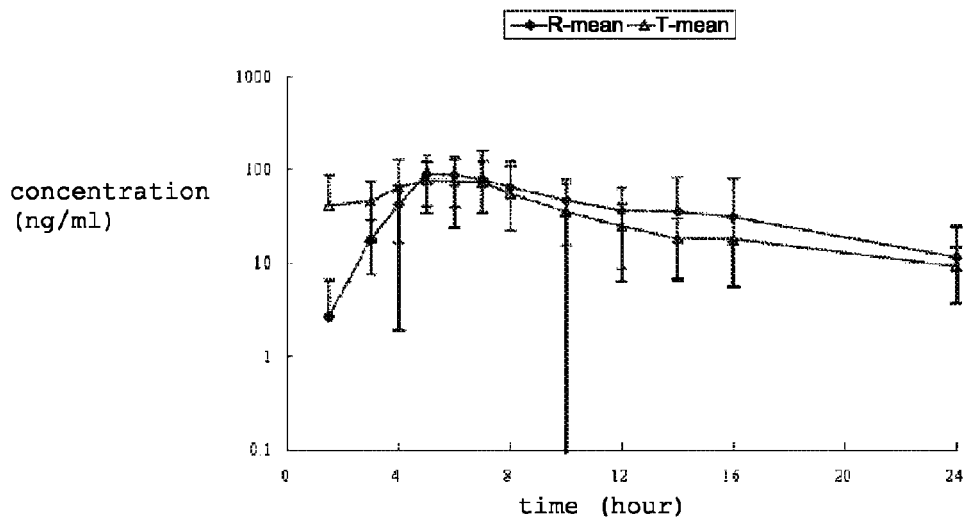
FIG. 10(B) shows the mean plasma concentration-time profile of carvedilol with the Log-Linear ordinate after subjects received the reference drug (Coreg™) (●R-Mean) and the T4 formulation (ΔT-Mean).

FIGS. 10(A) and 10(B) show the mean plasma concentration-time profiles of carvedilol after subjects received Coreg™ and the T4 formulation. These results show that the T4 Formulation provides an immediate loading dose of carvediolol, extends the duration of carvedilol release and maintains an adequate plasma concentration for at least 24 hours.

What is claimed is:

1. A controlled release formulation comprising, two or more subunits wherein at least one of said subunits is an immediate release carvedilol subunit comprising a therapeutically effective amount of carvedilol free base or carvedilol salt thereof, a matrix forming polymer, and a pharmaceutically acceptable carrier, and wherein at least one of said subunits is a slow release carvedilol subunit comprising a therapeutically effective amount of carvedilol free base or carvedilol salt thereof, a matrix forming polymer, a solubility enhancer and a pharmaceutically acceptable carrier, wherein the matrix forming polymer comprises ethycellulose having an ethoxyl content of about 20% to about 80% (w/w), or the matrix forming polymer comprises hydroxyethylmethylcellulose (HEMC) having a methoxyl content of from about 10% to about 60% (w/w).

2. The controlled release formulation of claim 1 wherein the carvedilol is carvedilol free base.

3. The controlled release formulation according to claim 1, wherein the solubility enhancer comprises one or more of the following: hydroxypropyl cellulose (HPC), hydroxyethyl cellulose (HEC), polyvinylpyrrolidone (PVP), polyethylene glycol (PEG), or sodium lauryl sulfate (SLS).

4. The controlled release formulation according to claim 1, wherein the pharmaceutically acceptable carrier comprises one or more of the following: lactose, corn starch or magnesium stearate.

5. The controlled release formulation according to claim 1, wherein the controlled release formulation exhibits a ratio of a geometric mean of logarithmic transformed $AUC_{0-\infty}$ of the controlled release formulation to a geometric mean of logarithmic transformed $AUC_{0-\infty}$ of a reference drug (Coreg CR™) of about 0.80 to about 1.20; or wherein the controlled release formulation exhibits a ratio of a geometric mean of logarithmic transformed $AUC_{0-t}$ of the controlled release formulation to a geometric mean of logarithmic transformed $AUC_{0-t}$ of a reference drug (Coreg CR™) of about 0.80 to about 1.20; or wherein the controlled release formulation exhibits a ratio of a geometric mean of logarithmic transformed $C_{max}$ of the controlled release formulation to a geometric mean of logarithmic transformed $C_{max}$ of a reference drug (Coreg CR™) of about 0.80 to about 1.20.

6. The controlled release formulation according to claim 3, wherein the controlled release formulation exhibits a first peak plasma $T_{max1}$ of about 4 hours, and a second peak plasma $T_{max2}$ of about 24 hours after oral administration to a patient.

7. A controlled release formulation, comprising:
  A. One or more immediate release subunits, comprising;
    (i) a therapeutically effective amount of carvedilol free base or carvedilol salt thereof;
    (ii) about 4% to about 5% by weight of a matrix forming polymer comprising one or more of the following: hydroxypropyl methylcellulose (HPMC), polyethylene oxide, alginate, methylcellulose, ethycellulose, a methacrylic copolymer, or hydroethylmethylcellulose (HEMC); and
    (iii) about 0.01% to about 0.1% by weight of an excipient; and
  B. one or more slow release subunits, comprising;
    (i) a therapeutically effective amount of carvedilol free base or carvedilol salt thereof;
    (ii) about 20% to about 55% by weight of a matrix forming polymer comprising one or more of the following: hydroxypropyl methylcellulose (HPMC), polyoxethylene oxide, alginate, methylcellulose, ethycellulose, a methacrylic copolymer, or hydroethylmethylcellulose (HEMC);
    (iii) about 1.0% to about 30% by weight of a solubility enhancer comprising one or more of the following: hydroxypropyl cellulose (HPC), hydroxyethyl cellulose (HEC), polyvinylpyrrolidone (PVP), polyethylene glycol (PEG), or sodium lauryl sulfate (SLS); and
    (iv) about 0.01% to about 25% by weight of an excipient.

8. The controlled release formulation according to claim 7, wherein carvedilol is carvedilol free base.

9. The controlled release formulation of claim 7, wherein ethycellulose contains about 20% to about 80% (w/w) of ethoxyl.

10. The controlled release formulation of claim 7, wherein the methoxyl content of the hydroethylmethylcelluose (HEMC) is from about 10% to about 60% (w/w).

11. The controlled release formulation according to claim 7, wherein the excipient comprises one or more of the following: lactose, corn starch, or magnesium stearate.

12. The controlled release formulation according to claim 7, wherein the controlled release formulation exhibits a ratio of a geometric mean of logarithmic transformed $AUC_{0-\infty}$ of the controlled release formulation to a geometric mean of logarithmic transformed $AUC_{0-\infty}$ of a reference drug (Coreg CR™) of about 0.80 to about 1.20;

wherein the controlled release formulation exhibits a ratio of a geometric mean of logarithmic transformed $AUC_{0-t}$ of the controlled release formulation to a geometric mean of logarithmic transformed $AUC_{0-t}$ of a reference drug (Coreg CR™) of about 0.80 to about 1.20; or wherein the controlled release formulation exhibits a ratio of a geometric mean of logarithmic transformed $C_{max}$ of the controlled release formulation to a geometric mean of logarithmic transformed $C_{max}$ of a reference drug (Coreg CR™) of about 0.80 to about 1.20.

13. The controlled release formulation according to claim 7, wherein the controlled release formulation exhibits a first peak plasma $T_{max1}$ of about 4 hours, and a second peak plasma $T_{max2}$ of about 24 hours after oral administration to a patient.

14. A controlled release formulation, which is selected from the group consisting of:
   (i) a formulation comprising
   (a) an immediate release subunit, comprising 2.9% by weight of carvedilol free base or a pharmaceutically acceptable salt thereof, 4.8% by weight of HPMC K100LV, and 11.3% by weight of lactose; and
   (b) an slow release subunit, comprising 9.1% by weight of carvedilol free base or a pharmaceutically acceptable salt thereof, 22.8% by weight of HPMC K15M, 26.2% by weight of PVP, and 22.8% by weight of corn starch;
   (ii) a formulation comprising
   (a) an immediate release subunit, comprising 2.7% by weight of carvedilol free base or a pharmaceutically acceptable salt thereof, 4.5% by weight of HPMC K100LV, 10.6% by weight of lactose and 0.05% by weight of magnesium stearate; and
   (b) an slow release subunit, comprising 8.6% by weight of carvedilol free base or a pharmaceutically acceptable salt thereof, 53.6% by weight of HPMC K15M, 1.8% by weight of SLS, and 17.9% by weight of corn starch; and
   (iii) a formulation comprising
   (a) an immediate release subunit, comprising 1.2% by weight of carvedilol free base or a pharmaceutically acceptable salt thereof, 4.2% by weight of HPMC K100LV, and 10.1% by weight of lactose; and
   (b) an slow release subunit, comprising 8.6% by weight of carvedilol free base or a pharmaceutically acceptable salt thereof, 35.7% by weight of HPMC K15M, 21.3% by weight of PVP, and 18.6% by weight of corn starch.

* * * * *